US00RE43618E

(19) United States
(12) Reissued Patent
Palti

(10) Patent Number: US RE43,618 E
(45) **Date of Reissued Patent: *Aug. 28, 2012**

(54) METHOD AND APPARATUS FOR DESTROYING DIVIDING CELLS

(75) Inventor: Yoram Palti, Haifa (IL)

(73) Assignee: Novocure Ltd, St. Helier, NJ (US)

( * ) Notice: This patent is subject to a terminal disclaimer.

(21) Appl. No.: 12/199,498

(22) Filed: Aug. 27, 2008

Related U.S. Patent Documents

Reissue of:
(64) Patent No.: 7,333,852
Issued: Feb. 19, 2008
Appl. No.: 10/204,334
PCT Filed: Feb. 16, 2001
PCT No.: PCT/IB01/00202
§ 371 (c)(1),
(2), (4) Date: Oct. 16, 2002
PCT Pub. No.: WO01/60994
PCT Pub. Date: Aug. 23, 2001

U.S. Applications:
(60) Provisional application No. 60/183,295, filed on Feb. 17, 2000.

(51) Int. Cl.
*A61N 1/00* (2006.01)
(52) U.S. Cl. ..... 607/2
(58) Field of Classification Search ..... 607/1–3, 607/101–103; 435/173.7, 173.4
See application file for complete search history.

(56) References Cited

U.S. PATENT DOCUMENTS 2,220,269 A 11/1940 Patzold et al.
3,991,770 A 11/1976 LeVeen
4,016,886 A 4/1977 Doss et al.
4,121,592 A 10/1978 Whalley
4,263,920 A 4/1981 Tasto et al.
4,467,809 A 8/1984 Brighton
4,472,506 A 9/1984 Liburdy
4,622,952 A 11/1986 Gordon
4,626,506 A 12/1986 Zimnermann et al.
4,676,258 A 6/1987 Inokuchi et al.
4,822,470 A 4/1989 Chang
4,846,178 A 7/1989 Fuxue et al.
(Continued)

FOREIGN PATENT DOCUMENTS

EP 0 330 797 A2 9/1989
(Continued)

OTHER PUBLICATIONS

Hofmann et al., "Electronic Genetic-Physical and Biological Aspects of Cellular Electomanipulation", IEEE Eng. in Med. and Biology Mag., Dec. 1986, p. 6-23, New York.

(Continued)

*Primary Examiner* — George Evanisko
(74) *Attorney, Agent, or Firm* — Proskauer

(57) ABSTRACT

The present invention provides a method and apparatus for selectively destroying dividing cells in living tissue formed of dividing cells and non-dividing cells. The dividing cells contain polarizable intracellular members and during late anaphase or telophase, the dividing cells are connected to one another by a cleavage furrow. According to the present method the living tissue is subjected to electric field conditions sufficient to cause movement of the polarizable intracellular members toward the cleavage furrow in response to a non-homogenous electric field being induced in the dividing cells. The non-homogenous electric field produces an increased density electric field in the region of the cleavage furrow. The movement of the polarizable intracellular members towards the cleavage furrow causes the break down thereof which results in destruction of the dividing cells, while the non-dividing cells of the living tissue remain intact.

20 Claims, 5 Drawing Sheets

U.S. PATENT DOCUMENTS

| | | | |
|---|---|---|---|
| 4,846,196 | A | 7/1989 | Wiksell et al. |
| 4,923,814 | A | 5/1990 | Marshall |
| 4,936,303 | A | 6/1990 | Derwiler et al. |
| 4,971,991 | A | 11/1990 | Umemura et al. |
| 5,099,756 | A | 3/1992 | Franconi et al. |
| 5,158,071 | A | 10/1992 | Umemura et al. |
| 5,236,410 | A | 8/1993 | Granov et al. |
| 5,269,304 | A | 12/1993 | Matthews |
| 5,312,813 | A | 5/1994 | Costerton et al. |
| 5,386,837 | A | 2/1995 | Sterzer |
| 5,389,069 | A | 2/1995 | Weaver |
| 5,441,532 | A | 8/1995 | Fenn |
| 5,441,746 | A | 8/1995 | Chagnon |
| 5,468,223 | A | 11/1995 | Mir |
| 5,606,971 | A | 3/1997 | Sarvazyn |
| 5,674,267 | A | 10/1997 | Mir et al. |
| 5,718,246 | A | 2/1998 | Vona |
| 5,807,257 | A | 9/1998 | Bridges |
| 5,964,726 | A | 10/1999 | Korenstein et al. |
| 5,976,092 | A | 11/1999 | Chinn |
| 5,984,882 | A | 11/1999 | Rosenschein et al. |
| 6,027,488 | A | 2/2000 | Hofmann et al. |
| 6,043,066 | A | 3/2000 | Mangano et al. |
| 6,055,453 | A | 4/2000 | Hofmann et al. |
| 6,068,650 | A | 5/2000 | Hofmann et al. |
| 6,096,020 | A | 8/2000 | Hofmann et al. |
| 6,319,901 | B1 | 11/2001 | Bernard et al. |
| 6,366,808 | B1 | 4/2002 | Schroeppel et al. |
| 6,413,255 | B1 | 7/2002 | Stern |
| 6,447,499 | B2 | 9/2002 | Gray |
| 6,856,839 | B2 | 2/2005 | Litovitz |
| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,146,210 | B2 | 12/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |
| 7,565,206 | B2 | 7/2009 | Palti |
| 2002/0193832 | A1 | 12/2002 | Gray |
| 2002/0193833 | A1 | 12/2002 | Dimmer et al. |
| 2003/0060856 | A1 | 3/2003 | Chornenky et al. |
| 2003/0191506 | A1 | 10/2003 | Shloznilov |
| 2004/0068296 | A1 | 4/2004 | Palti |
| 2005/0209640 | A1 | 9/2005 | Palti |
| 2005/0209641 | A1 | 9/2005 | Palti |
| 2005/0240173 | A1 | 10/2005 | Palti |
| 2005/0240228 | A1 | 10/2005 | Palti |
| 2006/0149341 | A1 | 7/2006 | Palti |
| 2006/0233867 | A1 | 10/2006 | Palti |
| 2006/0241547 | A1 | 10/2006 | Palti |
| 2006/0276858 | A1 | 12/2006 | Palti |
| 2006/0282122 | A1 | 12/2006 | Palti |
| 2007/0033660 | A1 | 2/2007 | Palti |
| 2007/0184020 | A1 | 8/2007 | Kalbe et al. |
| 2007/0225766 | A1 | 9/2007 | Palti |
| 2007/0239213 | A1 | 10/2007 | Palti |
| 2008/0221630 | A1 | 9/2008 | Palti |
| 2008/0319372 | A1 | 12/2008 | Palti |
| 2009/0043346 | A1 | 2/2009 | Palti |
| 2009/0076366 | A1 | 3/2009 | Palti |

FOREIGN PATENT DOCUMENTS

| | | | |
|---|---|---|---|
| EP | 0330797 | | 9/1989 |
| GB | 1 419 660 | A1 | 12/1975 |
| GB | 1419660 | | 12/1975 |
| GB | 2 026 322 | A1 | 2/1980 |
| GB | 2026322 | | 2/1980 |
| GB | 2 043 453 | A1 | 10/1980 |
| GB | 2043453 | | 10/1980 |
| WO | 0160994 | | 8/2001 |
| WO | WO 01/60994 | | 8/2001 |

OTHER PUBLICATIONS

Berg et al., "Electric Field Effects on Bilogical Membranes:Electoincorporation and Electofusion",Ettore Maj Inter. Science, 1987,p. 135-166,vol. 32,Phys. Science, New York.

Kirson et al., "Disruption of Cancer Cell Replication by Alternating Electric Fields", Cancer Research 64, May 2004, p. 3288-3295, Haifa, Israel.

Asbury et al., "Trapping of DNA in Nonuniform Oscillating Electric Fields", Biophysical Journal, Feb. 1998, p. 1024-1030, vol. 74,Seattle, WA.

Janigro et al., "Alternating current electrical stimulation enhanced chemotherapy: a novel strategy to bypass multidrug resistance in tumor cells", BMC Cancer, 2006, 6:72.

Giladi et al., Microbial Growth Inhibition by Alternating Electric Fields, Antimicrobial Agents and Chemotherapy, Oct. 2008, p. 3517-3522.

Search Report and Written Opinion from corresponding application PCT/US2008/002134.

U.S. Appl. No. 10/263,329, filed Oct. 2, 2002, Palti.

Palti, Oct. 31, 2002, Titled: Apparatus and Method for Treating a Tumor or the Like.

Palti, Nov. 4, 2002, Titled: Method and Apparatus for Destroying Tumor Cells.

METHOD AND APPARATUS FOR DESTROYING DIVIDING CELLS

Matter enclosed in heavy brackets [ ] appears in the original patent but forms no part of this reissue specification; matter printed in italics indicates the additions made by reissue.

*CROSS REFERENCE TO RELATED APPLICATIONS*

*This application is a §371 national stage of PCT/IB01/00202, filed Feb. 16, 2001, which claims the benefit of U.S. Provisional Application 60/183,295, filed Feb. 17, 2000.*

FIELD OF THE INVENTION

The present invention relates to selective destruction of rapidly dividing cells and, more particularly, to a method and device for selectively destroying dividing cells.

BACKGROUND OF THE INVENTION

It is known in the art that tumors, particularly malignant or cancerous tumors, grow very uncontrollably compared to normal tissue. Such expedited growth enables tumors to occupy an ever-increasing space and to damage or destroy tissue adjacent thereto. Furthermore, certain cancers are characterized by an ability to transmit cancerous "seeds", including single cells or small cell clusters (metastasises), to new locations where the metastatic cancer cells grow into additional tumors.

The rapid growth of tumors in general, and malignant tumors in particular, as described above, is the result of relatively frequent cell division or multiplication of these cells compared to normal tissue cells. The distinguishably frequent cell division of cancer cells is the basis for the effectiveness of existing cancer treatments, e.g., irradiation therapy and the use of various chemo-therapeutic agents. Such treatments are based on the fact that cells undergoing division are more sensitive to radiation and chemo-therapeutic agents than non-dividing dells. Because tumor cells divide much more frequently than normal cells, it is possible, to a certain extent, to selectively damage or destroy tumor cells by cells, it is possible, to a certain extent, to selectively damage or destroy tumor cells by radiation therapy and/or by chemotherapy. The actual sensitivity of cells to radiation, therapeutic agents, etc., is also dependent on specific characteristics of different types of normal or malignant cell type. Thus, unfortunately, the sensitivity of tumor cells is not sufficiently higher than that of many types of normal tissues. This diminishes the ability to distinguish between tumor cells and normal cells and, therefore, existing cancer treatments typically cause significant damage to normal tissues, thus limiting the therapeutic effectiveness of such treatments. Furthermore, the inevitable damage to other tissue renders treatments very traumatic to the patients and, often, patients are unable to recover from a seemingly successful treatment. Also, certain types of tumors are not sensitive at all to existing methods of treatment.

There are also other methods for destroying cells that do not rely on radiation therapy or chemotherapy alone. For example, ultrasonic and electrical methods for destroying tumor cells may be used in addition to or instead of conventional treatments. In the typical electrical method, electrical current is delivered to a region of the target tissue using electrodes that are placed in contact with the body of the patient. The applied electrical current destroys substantially all cells in the vicinity of the target tissue. Thus, this type of electrical method does not discriminate between different types of cells within the target tissue and results in the destruction of both tumor cells and normal cells.

In U.S. Pat. No. 6,043,066 ('066) to Mangano, a method and device are presented which enable discrete objects having a conducting inner core, surrounded by a dielectric membrane to be selectively inactivated by electric fields via irreversible breakdown of their dielectric membrane. One potential application for this is in the selection and purging of certain biological cells in a suspension. According to this patent, an electric field is applied for targeting selected cells to cause breakdown of the dielectric membranes of these tumor cells, while purportedly not adversely affecting other desired subpopulations of cells. The cells are selected on the basis of intrinsic or induced differences in a characteristic electroporation threshold. The differences in this threshold can depend upon a number of parameters, including the difference in cell size.

The method of the '066 patent is therefore based on the assumption that the electroporation threshold of tumor cells is sufficiently distinguishable from that of normal cells because of differences in cell size and differences in the dielectric properties of the cell membranes. Based upon this assumption, the larger size of many types of tumor cells makes these cells more susceptible to electroporation and thus, it may be possible to selectively damage only the larger tumor cell membranes by applying an appropriate electric field. One disadvantage of this method is that the ability to discriminate is highly dependent upon on cell type, for example, the size difference between normal cells and tumor cells is significant only in certain types of cells. Another drawback of this method is that the voltages which are applied may damage some of the normal cells and may not damage all of the tumor cells because the differences in size and membrane dielectric properties are largely statistical and the actual cell geometries and dielectric properties may vary significantly.

All living organisms proliferate by cell division, including tissue cultures, microorganisms (such as bacteria, mycoplasma, yeast, protozoa, and other single-celled organisms), fungi, algae, plant cells, etc. Dividing cells of organisms may be destroyed, or their proliferation controlled, by methods that are based on the sensitivity of the dividing cells of these organisms to certain agents. For example, certain antibiotics stop the multiplication process of bacteria The process of eukaryotic cell division is called "mitosis", which involves nine distinct phases (see Darnell et al, Molecular Cell Biology, New York: Scientific American Books, 1986, p. 149). During interphase, the cell replicates chromosomal DNA, which begins condensing in early prophase. At this point, centrioles (each cell contains 2) begin moving towards opposite poles of the cell. In middle prophase, each chromosome is composed of duplicate chromatids. Microtubular spindles radiate from regions adjacent to the centrioles, which are closer to their poles. By late prophase, the centrioles have reached the poles, and some spindle fibers extend to the center of the cell, while others extend from the poles to the chromatids. The cells them moves into metaphase, when the chromosomes move toward the equator of the cell and align in the equatorial plane. Next is early anaphase, during which time daughter chromatids separate from each other at the equator by moving along the spindle fibers toward a centromere at opposite poles. The cell begins to elongate along the axis of the pole; the pole-to-pole spindles also elongate. Late anaphase occurs when the daughter chromosomes (as they are not called) each reach their respective opposite poles. At this point, cytokinesis begins as the cleavage furrow begins to form at the equator of the cell. In other words, late anaphase is the point at which pinching of the cell membrane begins. During telophase, cytokinesis is nearly complete and the spindles disappear. Only a relatively narrow membrane connection joins the two cytoplasms. Finally, the membranes separate fully, cytokinesis is complete, and the cell returns to interphase.

In meisosis, the cell undergoes a second division, involving separation of sister chromosomes to opposite poles of the cell along spindle fibers, followed by formation of a cleavage furrow and cell division. However, this division is not preceded by chromosome replication, yielding a haploid germ cell.

Bacteria also divide by chromosome replication, followed by cell separation. However, the daughter chromosomes separate by attachment to membrane components; there is no visible apparatus that contributes to cell division as in eukaryotic cells.

What is needed in the art and has heretofore not been available is a method of killing dividing cells that better discriminates between dividing cells, including single-celled organisms, and non-dividing cells and is capable of selectively destroying the dividing cells or organisms with substantially no affect on the non-dividing cells or organisms.

SUMMARY OF THE INVENTION

The present invention provides a new method and apparatus for selectively destroying cells undergoing growth and division. This includes cells, particularly tumor cells, in living tissue and single-celled organisms. The method and apparatus of the present invention eliminate or control the growth of such living tissue or organisms.

A major use of the method and apparatus of the present invention is in treatment of tumors by selective destruction of tumor cells with substantially no affect on normal tissue cells and, thus, the invention is described below in the context of selective destruction of tumor cells. It should be appreciated however that, for the purpose of the description that follows, the term "cell" may also refer to single-celled organisms (eubacteria, bacteria, yeast, protozoa), multi-celled organisms (fungi, algae, mold), and plants as or parts thereof that are not normally classified as "cells". The method of the present invention enables selective destruction of tumor cells, or other organisms, by selective destruction of cells undergoing division in a way that is more effective and more accurate (e.g., more adaptable to be aimed at specific targets) than existing methods. Further, the method of the present invention causes minimal damage, if any, to normal tissue and, thus, reduces or eliminates many side-effects associated with existing selective destruction methods, such as radiation therapy and chemotherapy. The selective destruction of dividing cells in accordance with the method of the present invention does not depend on the sensitivity of the cells to chemical agents or radiation. Instead, the selective destruction of dividing cells is based on distinguishable geometrical characteristics of cells undergoing division, in comparison to non-dividing cells, regardless of the cell geometry of the type of cells being treated.

In an embodiment of the present invention, cell geometry-dependent selective destruction of living tissue is performed by inducing a non-homogenous electric field in the cells, as described below.

It has been observed by the present inventor that, while different cells in their non-dividing state may have different shapes, e.g., spherical, ellipsoidal, cylindrical, "pancake" like, etc., the division process of practically all cells is characterized by development of a "cleavage furrow" in late anaphase and telophase. This cleavage furrow is a slow constriction of the cell membrane (between the two sets of daughter chromosomes) which appears microscopically as a growing cleft (e.g., a groove or a notch) that gradually separates the cell into two new cells. During this division process, there is a transient period (telophase) during which the cell structure is basically that of two sub-cells interconnected by a narrow "bridge" formed of the cell material. The division process is completed when the "bridge" between the two sub-cells is broken. The selective destruction of tumor cells in accordance with an embodiment of the present invention utilizes this unique geometrical feature of dividing cells, as described below.

When a cell or a group of cells are under natural conditions or environment, i.e., part of a living tissue, they are disposed surrounded by a conductive environment consisting mostly of an electrolytic inter-cellular fluid and other cells that are composed mostly of an electrolytic intra-cellular liquid. When an electric field is induced in the living tissue, by applying an electric potential across the tissue, an electric field is formed in the tissue having and the specific distribution and configuration of the electric field lines defines the paths of electric currents in the tissue, if currents are in fact induced in the tissue. The distribution and configuration of the electric field is dependent on various parameters of the tissue, including the geometry and the electric properties of the different tissue components, and the relative conductivities, capacities and dielectric constants (that may be frequency dependent) of the tissue components.

For constant electric fields or alternating fields having relatively low frequencies, the dielectric properties of the various system components may be ignored in determining the field distribution. Therefore, as a first approximation, the tissue properties may be reasonably represented by the relative impedances or conductivities of the various tissue components. Under these conditions, the intercellular fluid and intracellular fluid both have a relatively low impedance, while the cell membrane has a very high impedance. Thus, under these conditions, only a fraction of the electric field lines, or currents generated by the electric field, may penetrate the cells. These field lines or currents may penetrate the cell through the part of the membrane closest to the pole generating the field or current. The currents then flow across the cell in generally uniform pattern, in response to a generally homogenous field inside the cell, and exit the cell through a portion of the cell membrane closest to the other pole.

The electric current flow pattern for cells undergoing division is very different and unique. Such cells include first and second sub-cells, namely, an "original" cell and a newly formed cell, that are connected by a cytoplasm "bridge" or "neck". The currents penetrate the first sub-cell through the part of the membrane the current source pole; however, they do not exit the first sub-cell through a portion of its membrane closer to the opposite pole (i.e., the current sink). Instead, the lines of current flow converge at the neck or cytoplasm bridge, whereby the density of the current flow lines is greatly increased. A corresponding, "mirror image", process takes place in the second sub-cell, whereby the current flow lines diverge to a lower density configuration as they depart from the bridge, and finally exit the second sub-cell from a part of its membrane closest to the current sink.

It is well known that when an object with no net electric charge is placed in a homogeneous electric field, although the object may be polarized, no net electric forces act upon it. However, when such an object is placed in a non-uniform converging or diverging field, electric forces act on it and pull it towards the higher density electric field lines. In the case of a dividing cell, electric forces are exerted in the direction of the cytoplasm bridge between the two cells. Since all intracellular organelles are polarizable, they are all forced towards the bridge between the two cells. The field polarity is irrelevant to the direction of the force and, therefore, an alternating electric field may be used to produce substantially the same effect. The electric forces acting on macromolecules or intracellular organelles and the consequent movement of such macromolecules or intracellular organelles, in response to a non-homogenous electric field, is known in the art.

The movement of the cellular organelles towards the bridge disrupts the cell structure and results in increased pressure in the vicinity of the connecting bridge membrane. This pressure of the organelles on the bridge membrane is expected to break the bridge membrane and, thus, it is expected that the dividing cell will "explode" in response to this pressure. The ability to break the membrane and disrupt other cell structures can be enhanced by applying a pulsating alternating electric field, rather than a steady alternating electric field. When a pulsating electric field is applied to the tissue, the forces exerted on the intracellular organelles has a "hammering" effect, whereby force pulses (or beats) are applied to the organelles numerous times per second, enhancing the movement of organelles of different sizes and masses towards the bridge (or neck) portion from both of the sub-cells, thereby increasing the probability of breaking the cell membrane at the bridge portion. The forces exerted on the intracellular organelles also affect the organelles themselves and may collapse or break the organelles.

It is noted, however, that for the electric field to be effective in breaking the dividing cells, it should be properly orientated relative to the geometry of the dividing cell. For example, a field normal to the axis of the bridge will not be effective. Therefore, for effectively destroying a high percentage of the dividing cells, in accordance with the present invention, the electric potential applied to the tumor tissue is preferably rotated relative to the tumor tissue. Alternatively, if the electric field is applied for a sufficiently long period of time, it is expected to eventually affect all dividing cells, because the cells, which are not spacially oriented, as epithelial cells, may constantly change their orientation during the division process or with multiple divisions. Discontinuous, e.g., periodical, application of the electric field over longer periods of time, e.g., on and off for a few hours, is also expected to destroy all tumor cells.

The normal cells that may be sensitive to the electric fields are those cells that undergo relatively frequent divisions. Such cells are present mainly in the hematopoietic system, the ovaries or testicles, certain skin layers and embryos. In such tissues, undesired destruction of normal cells may occur, as it does with traditional cancer treatments like chemotherapy and radiation. Therefore, in a preferred embodiment of the invention, the electric field is applied selectively to avoid regions of rapidly dividing normal cells, for example, by shielding or by localized application of electrodes. Shielding can be performed by means of a conducting material, such as copper, aluminum, steel, etc. Additionally or alternatively, the field may be selectively targeted to specific regions, e.g., by controlling the configuration of the field-inducing electrodes. Additionally or alternatively, the field may be controlled by active means, for example, by applying secondary fields of opposite polarities at the areas being protected, to cancel the effect of the primary electric field at the protected areas.

In an embodiment of the invention, electric fields may be generated in the body by placing metal electrodes over the desired areas, with or without making actual contact with the skin. If fields not associated with conductive currents are desired, the electrodes may be electrically insulated. Localized internal fields may be produced by introducing electrodes into the living tissue, e.g., by insertion through body cavities or by penetrating the surface of the body. By properly controlling the field polarities and potentials, electric fields can be controlled and directed or focused at a relatively high resolution so as to be effective only in the desired regions. Additionally, physical components such as waveguides may be used to direct the fields and to access specific sites that are known to contain tumors.

It should be appreciated that the present invention may also be used in applications other than treatment of tumors in a living body. In fact, the selective destruction in accordance with the present invention may be used in conjunction with any organisms that proliferate by division and multiplication, for example, tissue cultures, microorganisms such as bacteria, mycoplasma, protozoa, fungi, algae, plant cells, etc. Such organisms divide by the formation of a groove or cleft as described above. As the groove or cleft deepens, a narrow bridge is formed between the two parts of the organism, similar to the bridge formed between the sub-cells of dividing animal cells. Since such organisms are covered by a membrane having a relatively low electric conductivity, similar to an animal cell membrane described above, the electric field lines in a dividing organism converge at the bridge connecting the two parts of the dividing organism. The converging field lines result in electric forces that displace polarizable elements within the dividing organism.

DETAILED DESCRIPTION OF PREFERRED EMBODIMENTS THE INVENTION

Figure 1A:
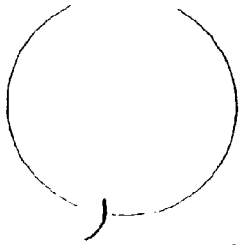
FIGS. 1A-1E are simplified, schematic, cross-sectional, illustrations of various stages of a cell division process.
Figure 1B:
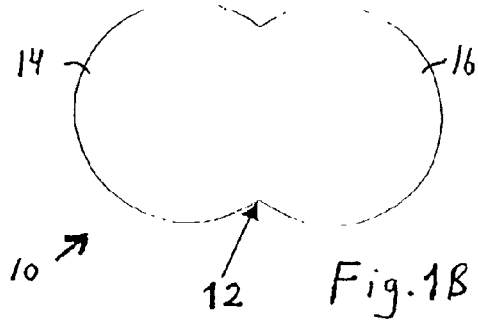
Figure 1C:
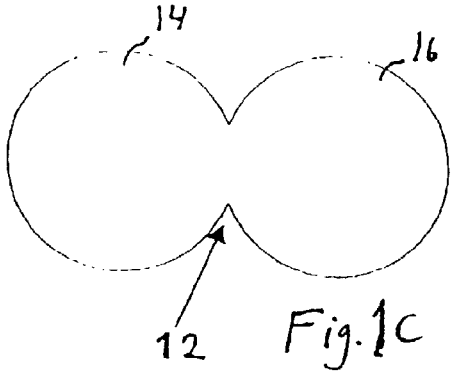
Figure 1D:
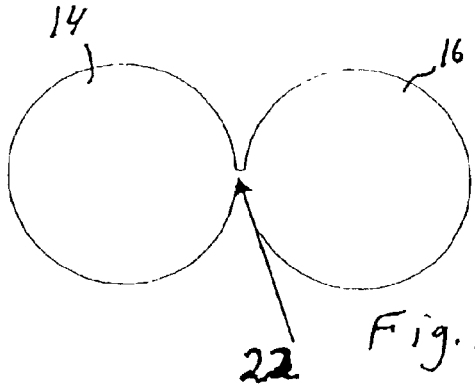

Reference is made to FIGS. 1A-1E which schematically illustrate various stages of a cell division process. FIG. 1A shows a cell 10 at its normal geometry, which may be generally spherical (as shown in the drawings), ellipsoidal, cylindrical, "pancake" like, or any other cell geometry, as is known in the art. FIGS. 1B-1D show cell 10 during different stages of its division process, which results in the formation of two new cells 18 and 20, shown in FIG. 1E.

Figure 1E:
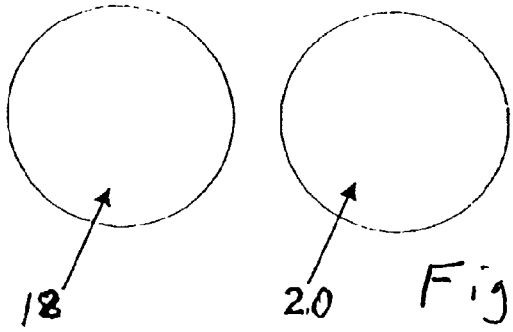

As shown in FIGS. 1B-1D, the division process of cell 10 is characterized by a slowly growing cleft 12 which gradually separates cell 10 into two units, namely, sub-cells 14 and 16, which eventually evolve into new cells 18 and 20 (FIG. 1E). As shown specifically in FIG. 1D, the division process is characterized by a transient period during which the structure of cell 10 is basically that of the two sub-cells 14 and 16 interconnected by a narrow "bridge" 22 containing cell material (cytoplasm surrounded by cell membrane).

Figure 2A:
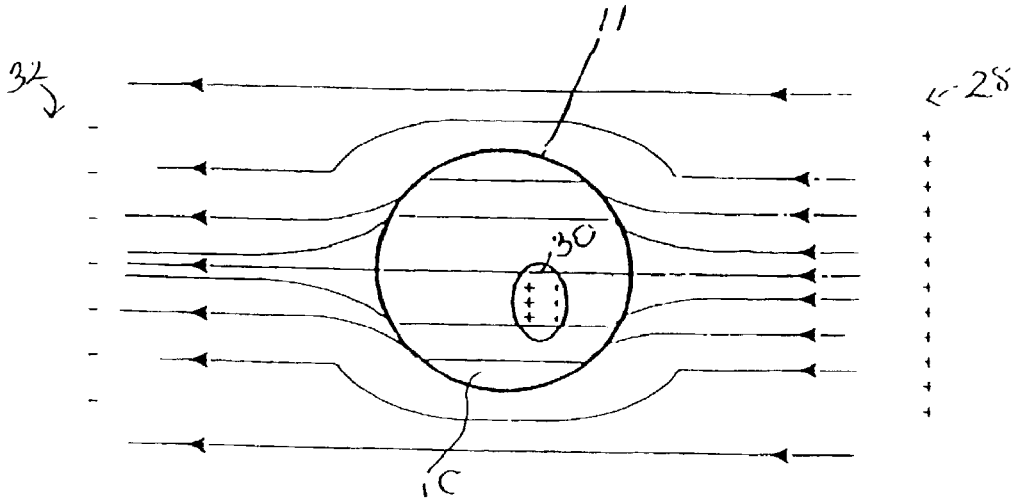
FIGS. 2A and 2B are schematic illustrations of a non-dividing cell being subjected to an electric field, in accordance with an embodiment of the present invention.
Figure 2B:
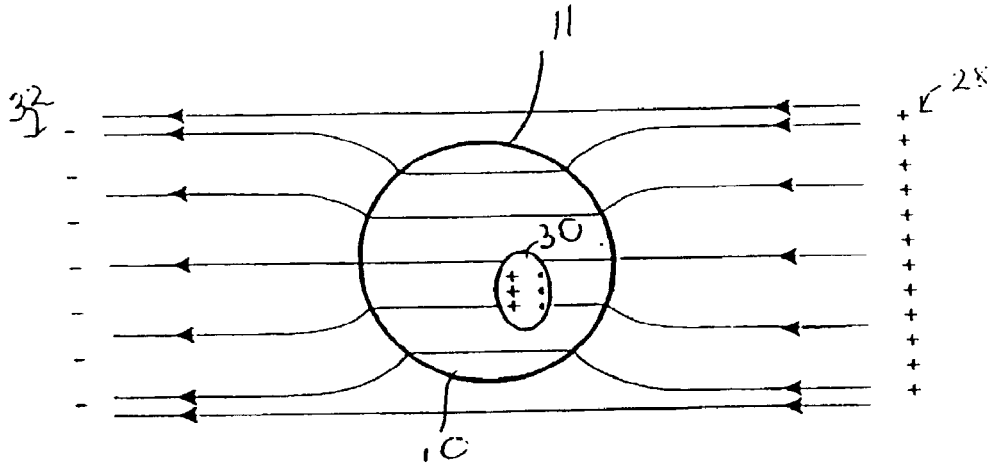

Reference is now made to FIGS. 2A and 2B, which schematically illustrate non-dividing cell 10 being subjected to an electric field produced by applying an alternating electric potential, at a relatively low frequency and at a relatively high frequency, respectively. Cell 10 includes intracellular organelles, e.g., a nucleus 30. Alternating electrical potential is applied across electrodes 28 and 32 that may be attached externally to a patient at a predetermined region, e.g., in the vicinity of a tumor being treated. When cell 10 is under natural conditions, i.e., part of a living tissue, it is disposed in a conductive environment (hereinafter referred to as: "volume conductor") consisting mostly of electrolytic inter-cellular liquid. When an electric potential is applied across electrode 28 and 32, some of the field lines of the resultant electric field (or the current induced in the tissue in response to the electric field) penetrate cell 10, while the rest of the field lines (or induced current) flow in the surrounding medium. The specific distribution of the electric field lines, which is substantially consistent with the direction of current flow in this case, depends on the geometry and the electric properties of the system components, e.g., the relative conductivities and dielectric constants of the system components, that may be frequency dependent. For low frequencies, e.g., frequencies considerably lower than 10 kHz, the conductance properties of the components dominate the current flow, and the field distribution is generally as depicted in FIG. 2A. At higher frequencies, e.g., at frequencies of between 10 kHz and 1 MHz, the dielectric properties of the components become more significant and eventually dominate the field distribution, resulting in field distribution lines as depicted generally in FIG. 2B.

For constant (i.e., DC) electric fields or relatively low frequency alternating electric fields, for example, frequencies under 10 kHz, the dielectric properties of the various components are not significant in determining and computing the field distribution. Therefore, as a first approximation, with regard to the electric field distribution, the system can be reasonably represented by the relative impedances of its various components. Under this approximation, the intercellular (i.e., extracellular) fluid and the intracellular fluid have a relatively low impedance, while the cell membrane 11 has a relatively high impedance. Thus, under low frequency conditions, only a fraction of the electric field lines (or currents induced by the electric field) penetrate membrane 11 of cell 10. At relatively high frequencies (e.g., 10 kHz-1 MHz), in contrast, the impedance of membrane 11 relative to the intercellular and intracellular fluids decreases and, thus, the fraction of currents penetrating the cells increases significantly. It should be noted that at very high frequencies, i.e., above 1 MHz, the membrane capacitance may short the membrane resistance and, therefore, the total membrane resistance may become negligible.

In any of the embodiments described above, the electric field lines (or induced currents) penetrate cell 10 from a portion of membrane 11 closest to one of the electrodes generating the current, e.g., closest to positive electrode 28 (also referred to herein as "source"). The current flow pattern across cell 10 is generally uniform because, under the above approximation. the field induced inside the cell is substantially homogenous. The currents exit cell 10 through a portion of membrane 11 closest to the opposite electrode, e.g., negative electrode 32 (also referred to herein as "sink").

The distinction between field lines and current flow may depend on a number of factors, for example, on the frequency of the applied electric potential and on whether electrodes 28 and 32 are electrically insulated. For insulated electrodes applying a DC or low frequency alternating voltage, there is practically no current flow along the lines of the electric field. At higher frequencies, displacement currents are induced in the tissue due to charging and discharging of the cell membranes (which act as capacitors to a certain extent), and such currents follow the lines of the electric field. Fields generated by non-insulated electrodes, in contrast, always generate some form of current flow, specifically, DC or low frequency alternating fields generate conductive current flow along the field lines, and high frequency alternating fields generate both conduction and displacement currents along the field lines. It should be appreciated, however, that movement of polarizable intracellular organelles according to the present invention (as described below) is not dependent on actual flow of current and, therefore, both insulated and non-insulated electrodes may be used efficiently in conjunction with the present invention. Nevertheless, insulated electrodes have the advantage of lower power consumption and causing less heating of the treated regions.

Figure 3A:
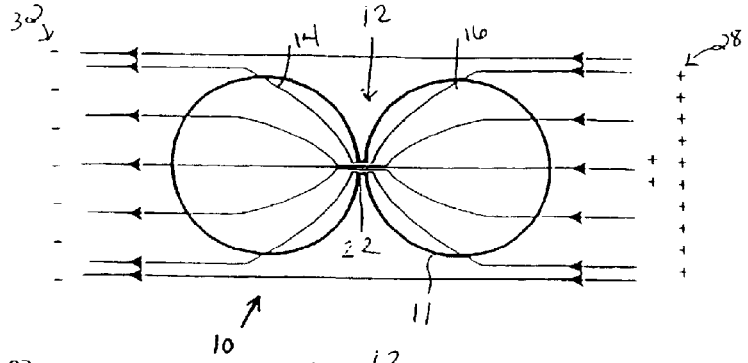
FIGS. 3A, 3B and 3C are schematic illustrations of a dividing cell being subjected to an electric field, resulting in destruction of the cell (FIG. 3C), in accordance with an embodiment of the present invention.
Figure 3B:
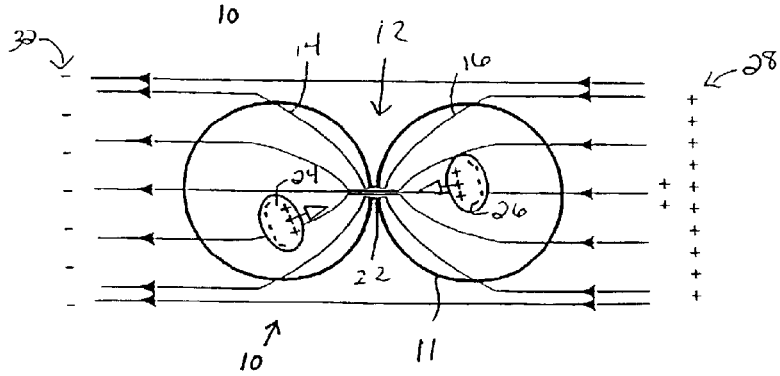
Figure 3C:
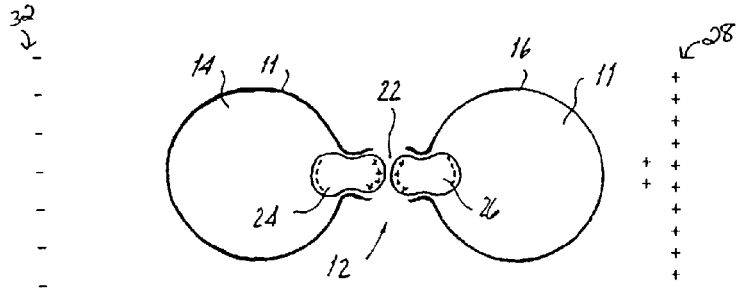

Reference is now made to FIGS. 3A-3C which schematically illustrate the electric current flow pattern in cell 10 during its division process, under the influence of high frequency alternating electric field in accordance with an embodiment of the invention. The field lines or induced currents penetrate cell 10 through a part of the membrane of sub-cell 16 closer to electrode 28. However, they do not exit through the cytoplasm bridge 22 that connects sub-cell 16 with the newly formed yet still attached sub-cell 14, or through a part of the membrane in the vicinity of bridge 22. Instead, the electric field or current flow lines—that are relatively widely separated in sub-cell 16—converge as they approach bridge 22 (also referred to as "neck" 22) and, thus, the current/field line density within neck 22 is increased dramatically. A "mirror image" process takes place in sub-cell 14, whereby the converging field lines in bridge 22 diverge as they approach the exit region of sub-cell 14.

It should be appreciated by persons skilled in the art that homogenous electric fields do not exert a force on electrically neutral objects, i.e., objects having substantially zero net charge, although such objects may become polarized. However, under a non-uniform, converging electric field, as shown in FIGS. 3A-3C, electric forces are exerted on polarized objects, moving them in the direction of the higher density electric field lines. In the configuration of FIGS. 3A and 3B, the direction of movement of polarized objects is towards the higher density electric filed lines, i.e., towards the cytoplasm bridge 22 between sub-cells 14 and 16. It is known in the art that all intracellular organelles, for example, nuclei 24 and 26 of sub-cells 14 and 16, respectively, are polarizable and, thus, such intracellular organelles will be electrically forced in the direction of bridge 22. Since the movement is always from the lower density currents to the higher density currents, regardless of the field polarity, the forces applied by the alternating electric field to organelles such as nuclei 24 and 26 are always in the direction of bridge 22. A comprehensive description of such forces and the resulting movement of macromolecules or intracellular organelles, a phenomenon referred to as dielectrophoresis, is described extensively in the literature, for example, in C. L. Asbury & G. van den Engh, Biophys. J. 74, 1024-1030, 1998, the disclosure of which is incorporated herein by reference.

The movement of organelles 24 and 26 towards bridge 22 disrupts the structure of the dividing cell and, eventually, the pressure of the converging organelles on bridge membrane 22 results in breakage of cell membrane 11 at the vicinity of bridge 22, as shown schematically in FIG. 3C. The ability to break membrane 11 at bridge 22 and to otherwise disrupt the cell structure and organization may be enhanced by applying a pulsating AC electric field, rather than a steady AC field. When a pulsating field is applied, the forces acting on organelles 24 and 26 may have a "hammering" effect, whereby pulsed forces beat on the intracellular organelles at a desired rhythm, e.g., a pre-selected number of times per second. Such "hammering" is expected to enhance the movement of intracellular organelles towards neck 22 from both sub cells 14 and 16), thereby increasing the probability of breaking cell membrane 11 in the vicinity of neck 22.

It is appreciated that the effectiveness of the field in causing the desired motion of the intracellular organelles is dependent on the orientation of the field relative to the dividing cell. For example, a field normal to the longitudinal axis of bridge 22 (i.e., normal to that shown in the drawings) will generally not be effective in destroying the cells. Therefore, in an embodiment of the present invention, the alternating electric potential applied to the tissue being treated is rotated relative to the tissue. Additionally or alternatively, those types of cells that randomly change the orientation of their division may be destroyed by applying an electric field for a sufficiently long period of time, or by repeating the application of the field periodically, e.g., in accordance with the cell-division cycle of the cells being destroyed, whereby the electric field lines eventually interact with all the dividing cells at an effective orientation. It is appreciated, however, that certain types of cells, e.g., epithelial cells, divide generally only in a specific orientation, and therefore, to effectively destroy such cells, the orientation of the field should be adjusted in accordance with the division orientation of the cells.

To demonstrate the expected effectiveness of electric fields in destroying tumor cells, following is an exemplary analysis of the effect of applying an electric field to a tumor which grows at a relatively moderate rate, e.g., a tumor that doubles its volume in 6 months from 1 $cm^3$ to 2 $cm^3$. In such a tumor, on the average, each cell divides every 20-30 minutes and each division is at its cleaving stage (FIGS. 1B-1D) for approximately 10-20 minutes. Thus, for example, an electric field applied to this tumor for a total time period of approximately two hours (which period may be divided into any number of sub-sessions), has a high probability of destroying practically all tumor cells, without damaging normal (i.e., non-dividing) cells in the vicinity of the tumor tissue. This expected result applies not only to the original tumor tissue, but also to metastases that may appear in various locations possessing similar qualities. Since the method of the present invention causes substantially no damage to non-dividing cells, this method may be used as a preventive treatment, to eliminate tumors before they are even detectable, whereby healthy tissue is not damage by redundant or unnecessary treatment.

It is appreciated that certain normal cells, e.g., cells in the hematopoietic system, the ovaries or testicles, skin and embryos, etc., undergo relative frequent divisions and, thus, may be sensitive to the electric fields. This situation also occurs with existing tumor treatments, such therapeutic irradiation or chemotherapy. Therefore, in an embodiment of the present invention, areas that include sensitive (i.e., frequently dividing) normal cells are selectively excluded from the regions covered by the electric fields, and/or shielded from the applied fields. Shielding may be preformed by positioning conducting materials, such as copper, aluminum, steel, etc., around the sensitive area to dissipate the electrical field. Additionally or alternatively, the field may be selectively applied to specific target regions, e.g., by controlling the configuration of the field-producing electrodes 28 and 30. Additionally or alternatively, the electrodes may be inserted into the body and brought to a vicinity of the target tissue, thereby producing a localized electric field in the vicinity of the cells being destroyed.

In an embodiment of the invention, electric fields may be generated in the body by placing metal electrodes over the desired areas, with or without actual contact with the skin. By properly controlling the field polarities and potentials, electric fields can be controlled and directed or focused at a relatively high resolution so as to be effective only in the desired regions. Additionally or alternatively, physical components such as wave-guides may be used to direct the fields and to access specific sites that are known to contain tumors.

Figure 4:
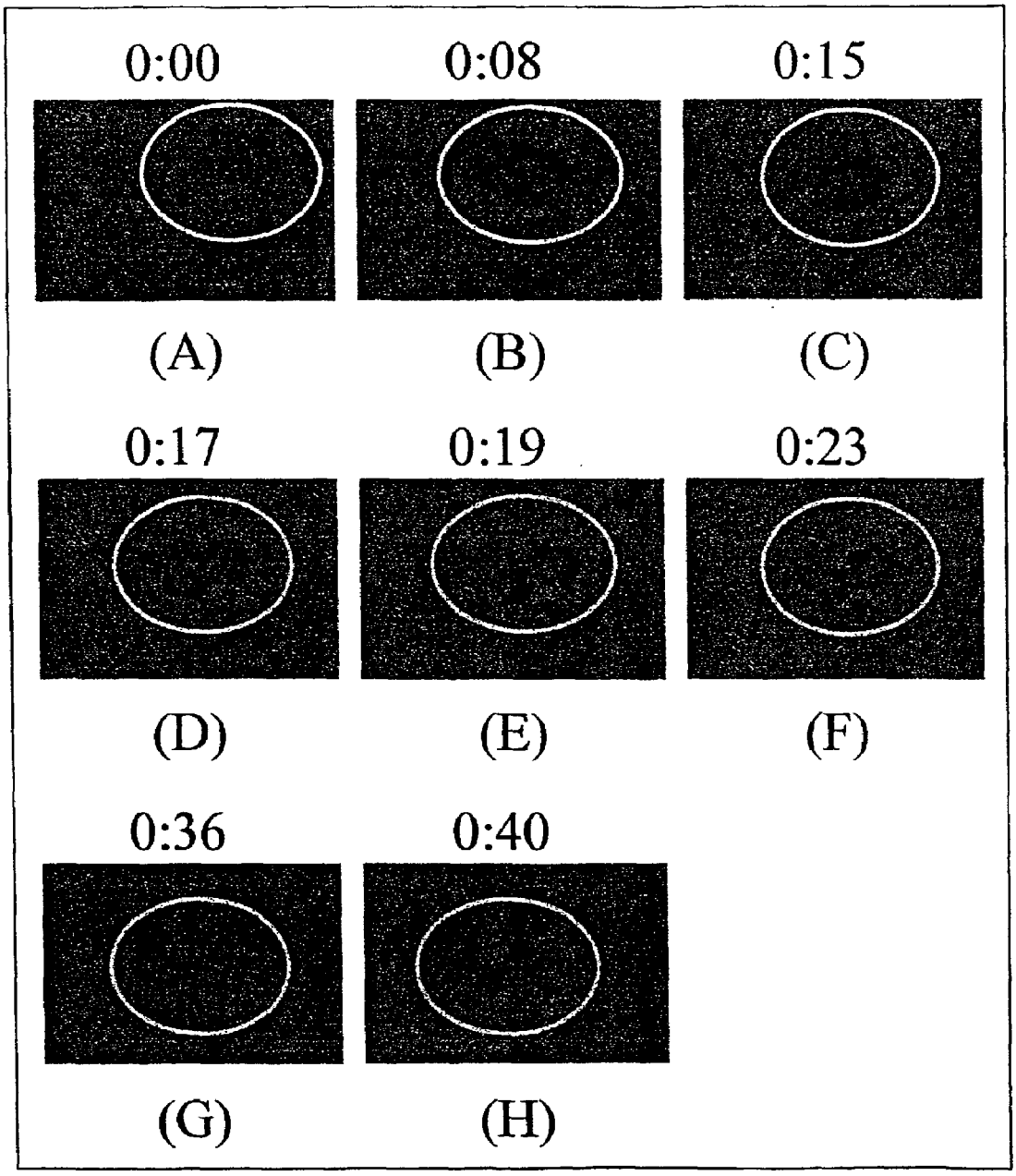
FIG. 4 is a series of sequential microphotographic frames taken over a set period of time illustrating a typical cell division process.

FIG. 4 presents a number of sequential microphotographic frames taken over a predetermined time period showing typical cell division when no electric field is applied. In this embodiment, the cells are BHK (baby hamster kidney) cells. The microphotography was taken over a 40 minute period. The cells were cultured in a standard culture medium (DMEM). Time is given above each photograph in terms of hours and minutes (hr:min). The photographs are magnified 500× to show the cell division more clearly. An ellipse is provided in each photograph to mark an area of interest. Frame A shows the location of a dividing cell prior to the division process. A non-dividing cell is normally flattened on the tissue culture plate. In this state, the cell can not be distinguished from the neighboring cells in the photographic frame. In frame B, the cell can be seen as it prepares itself for division and takes on a more spherical shape. As the cell assumes this general shape, the cell is more clearly distinguishable from the neighboring cells. As the division process continues, the dividing cell forms a cleft shown in frame C and proceeds to take on an hourglass-like shape, as shown in frame D. In frame E, the dividing cell splits into two separate cells and the cells move away from each other in frame F. The daughter cell begins to flatten in frame G and eventually disappear in frame H.

Figure 5:
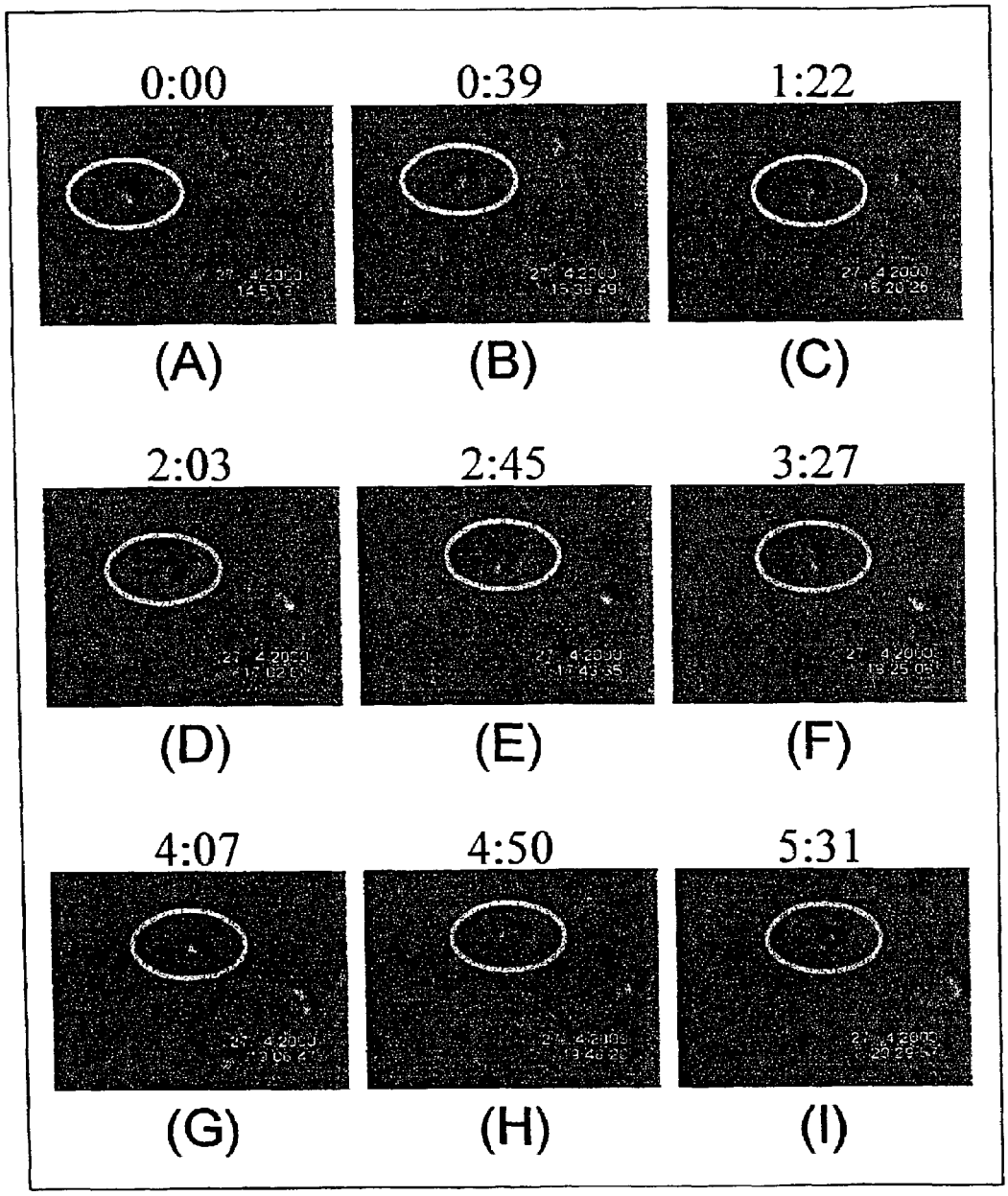
FIG. 5 is a series of sequential microphotographic frames illustrating a dividing cell being subjected to an electric field according to the method of the present invention, resulting in the cell being unable to complete the division process.

FIG. 5 presents a number of sequential microphotographic frames taken over a predetermined time period illustrating the application of the method of the present invention. More specifically, FIG. 5 shows the arrested division of BHK cells when an electrical field according to the present invention is applied for a limited predetermined period of time. In this example, the microphotography was taken over a period of 6 hours, while the electric field was activated for the first 1 hour and 40 minutes. The cells were grown in a standard tissue culture medium. The intensity of the electric field was 78 V/cm and the frequency was 100 KHz. Once again, time is given above each photographic frame in terms of hour and minute (hr:min). In this example, the magnification is on the order of 250× and an ellipse is provided to mark an area of interest.

Frame A is taken as the electric field is applied and shows a cell in the process of dividing. The cell is bulging from the plate and has a cleft. After almost 40 minutes, when one would expect the division process to be complete, the cell, shown in frame B, is maintaining its spherical shape and the cleft identified in the discussion of FIG. 4 cannot be identified at this point. After an additional 40 minute period, the dividing cell, as shown in frame C, is unable to complete the division process. About 20 minutes after the electric field is inactivated, frame D is taken. In this frame, the dividing cell is still in its division process and has taken on a generally hourglass-like shape. Subsequent frames E through I (taken at 40 minute intervals) show that the cell maintains the generally hourglass-like shape for the remainder of the filming session (3 hours) and in unable to complete the division process.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Because each of these tumors undergoes rapid growth, any one can be treated in accordance with the invention. The invention is particularly advantageous for treating brain tumors, which are difficult to treat with surgery and radiation, and often inaccessible to chemotherapy or gene therapies. In addition, the present invention is suitable for use in treating skin and breast tumors because of the ease of localized treatment provided by the present invention.

In addition, the present invention can control uncontrolled growth associated with non-malignant or pre-malignant conditions, and other disorders involving inappropriate cell or tissue growth by application of an electic field in accordance with the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplated.

Furthermore, undesirable fibroblast and endothelial cell proliferation associated with wound healing, leading to scar and keloid formation after surgery or injury, and restenosis after angioplasty can be inhibited by application of an electric field in accordance with the present invention. The non-invasive nature of this invention makes it particularly desirable for these types of conditions, particularly to prevent development of internal scars and adhesions, or to inhibit restenosis of coronary, carotid, and other important arteries.

Thus, the present invention provides an effective, simple method of selectively destroying dividing cells, e.g., tumor cells and parasitic organisms, while non-dividing cells or organisms are left affected by application of the method on living tissue containing both types of cells or organisms. Thus, unlike many of the conventional methods, the present invention does not damage the normal cells or organisms. In addition, the present invention does not discriminate based upon cell type (e.g., cells having differing sizes) and therefore may be used to treat any number of types of sizes having a wide spectrum of characteristics, including varying dimensions.

It will be appreciated by persons skilled in the art that the present invention is not limited to the embodiments described thus far with reference to the accompanying drawing. Rather the present invention is limited only by the following claims.

What is claimed is:

1. A method for selectively destroying dividing cells in living tissue, the dividing cells having polarizable intracellular members, the method comprising the steps of:

passing a first *alternating* electric field through the living tissue to produce a non-homogenous electric field within the dividing cells with an increased density in a region of a cleavage furrow in late anaphase or telophase, the non-homogenous electric field [being] *having a* sufficient *electric field strength* to move the polarizable intracellular members toward the cleavage furrow until the intracellular members disrupt the cleavage furrow, wherein the passing step is implemented for one or more intervals of time that are collectively sufficient for the disruptions of the cleavage furrow to destroy a significant portion of the dividing cells in the living tissue, and wherein passage of the first electric field through non-dividing cells in the living tissue leaves the nondividing cells substantially undamaged.

2. A method according to claim 1, wherein the cleavage furrow is in the form of a cytoplasm bridge membrane.

3. A method according to claim 1, wherein the first electric field has a sufficient frequency so that the non-homogenous electric field produced in the dividing cells defines electric field lines which generally converge at a region of the cleavage furrow, thereby defining the increased density electric field.

4. A method according to claim 1, wherein the passing step comprises the step of:

subjecting the living tissue to an alternating electric potential at a sufficient frequency to cause associated electric field lines to penetrate the dividing cells and form the non-homogenous electric field within the dividing cells.

5. A method according to claim 1, wherein the non-homogenous electric field generates electric forces in the dividing cells which act to pull the polarizable intracellular members toward the increased density electric field region.

6. A method according to claim 1, wherein the polarizable intracellular members are organelles.

7. A method according to claim 1, wherein the passing step comprises the step of:

subjecting the living tissue to a pulsating alternating electric potential at a sufficient frequency to form the non-homogenous electric field within the dividing cells.

8. A method according to claim 1, wherein the passing step comprises the step of:

subjecting the living tissue to an alternating electric potential at a frequency of between about 10 kHz and about 1 MHz.

9. A method according to claim 1, wherein the dividing cells comprise a first sub-cell and a second sub-cell with the cleavage furrow connecting the two in late anaphase or telophase.

10. A method according to claim 1, wherein the passing step comprises the step of:

providing a first electrode;

providing a second electrode;

applying an alternating electric potential across the first and second electrodes, wherein the first and second electrodes are disposed in a vicinity of the living tissue to be treated.

11. A method according to claim 1 further comprising the step of:

rotating a source of the first electric field relative to the living tissue.

12. A method according to claim 1, wherein movement of the intracellular members toward the cleavage furrow increases pressure being exerted on the cleavage furrow, the increased pressure causing the region of the cleavage furrow to expand resulting in the cleavage furrow breaking apart and causing destruction of the dividing cells.

13. A method according to claim 1, wherein the living tissue is subjected to the first electric field for a predetermined period of time.

14. A method according to claim 13, wherein the predetermined period of time is less than about 2 hours.

15. A method according to claim 1, further comprising:

removing the first electric field for a predetermined period of time; and resubjecting the living tissue to the first electric field after the predetermined period of time has passed.

16. A method according to claim 1, wherein the first electric field is a substantially uniform electric field.

17. A method according to claim 1, wherein the passing step is continued for one or more intervals of time that collectively comprise at least two hours.

[18. A method for selectively destroying dividing cells in living tissue, the dividing cells containing polarizable intracellular members, the method comprising the step of:

passing an electric field through the living tissue to create conditions in dividing cells in late anaphase or telophase which are sufficient to cause displacement of the polarizable intracellular members towards a cleavage furrow connecting the dividing cells in response to a non-homogenous electric field being induced in the dividing cells, wherein the passing step is continued for one or more intervals of time that are collectively sufficient to permit the displacement of the polarizable intracellular members to cause a break down of the cleavage furrow which results in the destruction of a significant portion of the dividing cells while non-dividing cells of the living tissue remain intact.]

[19. A method according to claim 18, wherein the passing step comprises the step of:

subjecting the living tissue to an alternating electric potential at a frequency of between about 10 kHz and about 1 MHz.]

[20. A method according to claim 18, wherein the passing step is continued for one or more intervals of time that collectively comprise at least two hours.]

21. A method for selectively destroying a dividing-cell organism, the organism containing polarizable intracellular members and being attached to one another in late anaphase or telophase with a cleavage furrow, the method comprising the step of:

passing an *alternating* electric field through the organism [to create] *at a frequency that induces a non-homogenous* electric field [conditions sufficient] *in the organism during late anaphase or telophase, the alternating electric field having a sufficient electric field strength* to cause displacement of the polarizable intracellular members towards the cleavage furrow [in response to a non-homogenous electric field being induced in the organism] *until the intracellular members disrupt the cleavage furrow*, wherein the electric field conditions are applied for one or more intervals of time that are collectively sufficient to permit the non-homogenous electric field produced within the dividing cells to cause the displacement of the polarizable intracellular members, to cause a break down of the cleavage furrow which results in destruction of the dividing organism.

22. A method according to claim 21, wherein the passing step is continued for one or more intervals of time that collectively comprise at least two hours.

*23. A method according to claim 1, wherein the alternating electric field has a frequency of about 100 kHz and an electric field strength of about 78 V/cm.*

* * * * *